(12) United States Patent
Loh et al.

(10) Patent No.: US 9,505,718 B2
(45) Date of Patent: Nov. 29, 2016

(54) 3-PIPERIDONE COMPOUNDS AND THEIR USE AS NEUROKININ-1 (NK1) RECEPTOR ANTAGONISTS

(71) Applicant: Nanyang Technological University, Singapore (SG)

(72) Inventors: Teck Peng Loh, Singapore (SG); Peng Wang, Singapore (SG); Jingmei Huang, Singapore (SG); Peng Fei Jackson Koh, Singapore (SG)

(73) Assignee: Nanyang Technological University, Singapore (SG)

( * ) Notice: Subject to any disclaimer, the term of this patent is extended or adjusted under 35 U.S.C. 154(b) by 0 days.

(21) Appl. No.: 14/777,392

(22) PCT Filed: Mar. 17, 2014

(86) PCT No.: PCT/SG2014/000130
§ 371 (c)(1),
(2) Date: Sep. 15, 2015

(87) PCT Pub. No.: WO2014/142761
PCT Pub. Date: Sep. 18, 2014

(65) Prior Publication Data
US 2016/0031817 A1 Feb. 4, 2016

Related U.S. Application Data

(60) Provisional application No. 61/791,217, filed on Mar. 15, 2013.

(51) Int. Cl.
C07D 211/00 (2006.01)
C07D 211/96 (2006.01)
C07D 211/02 (2006.01)

(52) U.S. Cl.
CPC .......... *C07D 211/96* (2013.01); *C07D 211/02* (2013.01)

(58) Field of Classification Search
None
See application file for complete search history.

(56) References Cited

U.S. PATENT DOCUMENTS 6,309,430 B1 10/2001 Paul
6,388,083 B2 5/2002 Lee et al.

FOREIGN PATENT DOCUMENTS

EP 0 528 495 A1 2/1993
WO 97/49710 A1 12/1997

OTHER PUBLICATIONS

Takahashi, Y. et al., Bioorg. Med. Chem. Lett. 2006 vol. 16, pp. 3813-3816.*
Achmatowicz et al., "Synthesis of methyl 2,3-dideoxy-DL-alk-2-enopyranosides from furan compounds," *Tetrahedron* 27:1973-1996, 1971.
Atobe et al., "Enantioselective Synthesis of Primary 1-(Aryl)alkylamines by Nucleophilic 1,2-Addition of Organolithium Reagents to Hydroxyoxime Ethers and Application to Asymmetric Synthesis of G-Protein-Coupled Receptor Ligands," *J. Org. Chem.* 69:5595-5607, 2004.
Bozell et al., "Technology development for the production of biobased products from biorefinery carbohydrates—the US Department of Energy's "Top 10" revisited," *Green Chem.* 12:539-554, 2010.
Calvez et al., "Stereoselective Synthesis of (2S,3S)-3-Hydroxy-2-phenylpiperidines, Precursors of Non-peptidic Substance P Antagonists," *Tetrahedron Letters* 40:7099-7100, 1999.
CAS Registry No. 1213779-04-4 (ID 6), SciFinder, Nov. 3, 2015, 4 pages.
CAS Registry No. 1273577-08-4 (ID 5), SciFinder, Nov. 3, 2015, 4 pages.
CAS Registry No. 1332590-88-1 (ID 4), SciFinder, Nov. 3, 2015, 4 pages.
CAS Registry No. 1367696-47-6 (ID 2), SciFinder, Nov. 3, 2015, 4 pages.
CAS Registry No. 148701-78-4 (ID 10), SciFinder, Nov. 3, 2015, 4 pages.
CAS Registry No. 200956-65-6 (ID 9), SciFinder, Nov. 3, 2015, 4 pages.
CAS Registry No. 244056-97-1 (ID 8), SciFinder, Nov. 3, 2015, 4 pages.
CAS Registry No. 898547-70-1 (ID 7), SciFinder, Nov. 3, 2015, 4 pages.
Cassidy et al., "An Aza-Achmatowicz Approach toward the Hydroxylated Piperidine Alkaloids (±)-Azimic Acid and (±)-Deoxocassine," *Organic Letters* 6(22):4029-4031, 2004.
Chheda et al., "Liquid-Phase Catalytic Processing of Biomass-Derived Oxygenated Hydrocarbons to Fuels and Chemicals," *Angew. Chem. Int. Ed.* 46:7164-7183, 2007.
Ciufolini et al., "Nitrogen Heterocycles From Furans: The Aza-Achmatowicz Reaction," *Synlett* 1998(2):105-114.
Clark et al., "Chapter 1: The Biorefinery Concept: An Integrated Approach," *Introduction to Chemicals from Biomass*, Second Edition, John Wiley & Sons, Ltd., 2015, 30 pages.
Corma et al., "Chemical Routes for the Transformation of Biomass into Chemicals," *Chem. Rev.* 107:2411-2502, 2007.
Desai et al., "Discovery of a Potent Substance P Antagonist: Recognition of the Key Molecular Determinant," *J. Med. Chem.* 35:4911-4913, 1992.
Gallezot, "Conversion of biomass to selected chemical products," *Chem. Soc. Rev.* 41:1538-1558, 2012.
Gardner et al., "GR205171: A novel antagonist with high affinity for the tachykinin $NK_1$ receptor, and potent broad-spectrum anti-emetic activity," *Regulatory Peptides* 65:45-53, 1996.
Garrido et al., "Enantioselective Synthesis of (+)-L-733,060 and (+)-CP-99,994: Application of an Ireland—Claisen Rearrangement/Michael Addition Domino Sequence," *Synlett* 2010(3):0387-0390.
Gaucher et al., "Concise Total Asymmetric Synthesis of (S)-2-Phenylpiperidin-3-one," *Synlett* 2009(20):3320-3322.

(Continued)

Primary Examiner — Heidi Reese
(74) Attorney, Agent, or Firm — Seed IP Law Group LLP

(57) ABSTRACT

The invention relates to 3-piperidone compounds, and in particular, to (2S)-phenyl-3-piperidone and its synthesis method. Use of the thus-synthesized 3-piperidone compounds as potent neurokinin-1 (NK1) receptor antagonists is also provided.

14 Claims, 4 Drawing Sheets

(56) References Cited

OTHER PUBLICATIONS

Georgiadis et al., "Products from Furans. 4.[1a] Selective Oxidation of 2-Furfuryl Alcohol Derivatives, in the Presence of Aryl Thioethers, with N-Bromosuccinimide (NBS). A New Procedure for the Preparation of 2H-Pyran-3(6H)-ones," *J. Org. Chem.* 51:2725-2727, 1986.

Gockel et al., "Golden Times for Allenes: Gold-Catalyzed Cycloisomerization of β-Hydroxyallenes to Dihydropyrans," *Organic Letters* 8(20):4485-4488, 2006.

Harris et al., "A Flexible Approach toward Trisubstituted Piperidines and Indolizidines: Synthesis of 6-epi-Indolizidine 223A," *J. Org. Chem.* 68, 4371-4381, 2003.

Harris et al., "Stereoselective Synthesis of 2,5,6-Trisubstituted Piperidines," *Organic Letters* 4(12):2029-2031, 2002.

Harrison et al., "Piperidine-Ether Based hNK$_1$ Antagonists 1: Determination of the Relative and Absolute Stereochemical Requirements," *Bioorganic & Medicinal Chemistry Letters* 4(21):2545-2550, 1994.

Haukaas et al., "Synthesis of D- and L-Deoxymannojirimycin via an Asymmetric Aminohydroxylation of Vinylfuran," *Organic Letters* 3(3):401-404, 2001.

Huang et al., "Asymmetric Synthesis of (+)-L-733, 060 and (+)-CP-99, 994 Based on a New Chiral 3-Piperidinol Synthon," *Organic Letters* 5(11):1927-1929, 2003.

Kabro et al., "Biomass Conversion to High Value Chemicals: From Furfural to Chiral Hydrofuroins in Two Steps," *Organic Letters* 14(15):4014-4017, 2012.

Karinen et al., "Biorefining: Heterogeneously Catalyzed Reactions of Carbohydrates for the Production of Furfural and Hydroxymethylfurfural," *ChemSusChem* 4:1002-1016, 2011.

Kokotos et al., "Hemiaminals as substrates for sulfur ylides: Direct asymmetric syntheses of functionalised pyrrolidines and piperidines," *Chem. Commun.* 2006:2156-2158.

Koulocheri et al., "1,4-Reductive Addition of Hydrazoic Acid to γ-Oxo-α,β-unsaturated δ-Lactones and -Lactams: A Convenient Route to α-Amino-γ-oxo-α,β-unsaturated δ-Lactones and -Lactams," *Eur. J. Org. Chem.* 1999:1449-1453.

Kramer et al., "Distinct Mechanism for Antidepressant Activity by Blockade of Central Substance P Receptors," *Science* 281:1640-1646, Sep. 1998.

Kulagowski et al., "Stereocontrolled Syntheses of Epimeric 3-Aryl-6-phenyl-1-oxa-7-azaspiro[4.5]decane NK-1 Receptor Antagonist Precursors," *Organic Letters* 3(5):667-670, 2001.

Kursanov et al., "Applications of Ionic Hydrogenation to Organic Synthesis," *Synthesis* 1974(9):633-651.

Ladduwahetty et al., "N-Heteroaryl-2-phenyl-3-(benzyloxy)piperidines: A Novel Class of Potent Orally Active Human NK$_1$ Antagonists," *J. Med. Chem.* 39:2907-2914, 1996.

Lancaster, "Chapter 6: Renewable Resources," *Green Chemistry: An Introductory Text*, Royal Society of Chemistry, Jan. 2002, 48 pages.

Lange et al., "Furfural—A Promising Platform for Lignocellulosic Biofuels," *ChemSusChem* 5:150-166, 2012.

Lee et al., "Asymmetric synthesis of (2S,3S)-3-hydroxy-2-phenylpiperidine via ring expansion," *Tetrahedron Letters* 42:6223-6225, 2001.

Leverett et al., "Application of the Aza-Achmatowicz Oxidative Rearrangement for the Stereoselective Synthesis of the Cassia and Prosopis Alkaloid Family," *J. Org. Chem.* 71:8591-8601, 2006.

Lewis et al., "Highly Stereoselective Approaches to α- and β-C-Glycopyranosides," *J. Am. Chem. Soc.* 104:4976-4978, 1982.

Lichtenthaler et al., "Carbohydrates as green raw materials for the chemical industry," *C. R. Chimie* 7:65-90, 2004.

Liu et al., "A General Approach to (5S,6R)-6-Alkyl-5-benzyloxy-2-piperidinones: Application to the Asymmetric Syntheses of Neurokinin Substance P Receptor Antagonist (−)-L-733,061 and (−)-Deoxocassine," *J. Org. Chem.* 69:6001-6009, 2004.

Maligres et al., "Stereocontrolled Preparation of a Nonpeptidal (−)-Spirobicyclic NK-1 Receptor Antagonist," *J. Org. Chem.* 67:1093-1101, 2002.

Martel et al., "Development of Agriculture Left-Overs: Fine Organic Chemicals from Wheat Hemicellulose-Derived Pentoses," *Top Curr Chem.* 294:79-115, 2010.

Melero et al., "Biomass as renewable feedstock in standard refinery units. Feasibility, opportunities and challenges," *Energy Environ. Sci.* 5:7393-7420, 2012.

Nelson et al., "Chapter 1: The Bioeconomy: A New Era of Products Derived from Renewable Plant-Based Feedstocks," *Plant Biomass Conversion*, Hood et al., (ed.), John Wiley & Sons Inc., 2011, 18 pages.

Pansare et al., "Synthesis of (+)-L-733,060, (+)-CP-99,994 and (2S,3R)-3-hydroxypipecolic acid: Application of an organocatalytic direct vinylogous aldol reaction," *Org. Biomol. Chem.* 10:2119-2125, 2012.

Ragauskas et al., "The Path Forward for Biofuels and Biomaterials," *Science* 311:484-490, Jan. 2006.

Rosen et al., "Synthesis and structure-activity relationships of CP-122,721, a second-generation NK-1 receptor antagonist," *Bioorganic & Medicinal Chemistry Letters* 8:281-284, 1998.

Searles et al., "Observation on the Synthesis of Allenes by Homologation of Alk-l-ynes," *J. Chem. Soc. Perkin Trans. I*:747-751, 1984.

Shishido et al., "Discovery and stereoselective synthesis of the novel isochroman neurokinin-1 receptor antagonist 'CJ-17,493'," *Bioorganic & Medicinal Chemistry* 16:7193-7205, 2008.

Srihari et al., "Total Synthesis of Both Enantiomers of Macrocyclic Lactone Aspergillide C," *Eur. J. Org. Chem.* 2011:6690-6697.

Takahashi et al., "A concise and practical catalytic asymmetric synthesis of (−)-CP-99,994 and (−)-L-733,061," *Tetrahedron Letters* 46:8927-8930, 2005.

Takahashi et al., "Novel γ-secretase inhibitors discovered by library screening of in-house synthetic natural product intermediates," *Bioorganic & Medicinal Chemistry Letters* 16:3813-3816, 2006.

Tokunaga et al., "C$_2$-Symmetric Bicyclo[2.2.2]octadienes as Chiral Ligands: Their High Performance in Rhodium-Catalyzed Asymmetric Arylation of N-Tosylarylimines," *J. Am. Chem. Soc.* 126:13584-13585, 2004.

Tuck et al., "Valorization of Biomass: Deriving More Value from Waste," *Science* 337:695-701, Aug. 2012.

U.S. Department of Energy, "Top Value Added Chemicals from Biomass: vol. I—Results of Screening for Potential Candidates from Sugars and Synthesis Gas" Werpy et al., (eds.), Aug. 2004, 77 pages.

Wallace et al., "A Double Ring Closing Metathesis Reaction in the Rapid, Enantioselective Synthesis of NK-1 Receptor Antagonists," *Organic Letters* 3(5):671-674, 2001.

Ward et al., "Discovery of an Orally Bioavailable NK$_1$ Receptor Antagonist, (2S,3S)-(2-Methoxy-5-tetrazol-1-ylbenzyl)(2-phenylpiperidin-3-yla)amine (GR203040), with Potent Antiemetic Activity," *J. Med. Chem.* 38:4985-4992, 1995.

Watanabe et al., "Pharmacological Characterization of T-2328, 2-Fluoro-4'-methoxy-3'-[[[(2S,3S)-2-phenyl-3-piperidinyl]amino]methyl]-[1,1'-biphenyl]-4-carbonitrile Dihydrochloride, as a Brain-Penetrating Antagonist of Tachykinin NK$_1$ Receptor," *J Pharmacol Sci* 106:121-127, 2008.

Williams et al., "Spirocyclic NK$_1$ Antagonists II: [4.5]-Spiroethers," *Bioorganic & Medicinal Chemistry Letters* 12:2719-2722, 2002.

Xing et al., "Production of furfural and carboxylic acids from waste aqueous hemicellulose solutions from the pulp and paper and cellulosic ethanol industries," *Energy Environ. Sci.* 4:2193-2205, 2011.

Zeitsch, *the chemistry and technology of furfural and its many by-products*, Elsevier, New York, 2000, 375 pages.

\* cited by examiner

3-PIPERIDONE COMPOUNDS AND THEIR USE AS NEUROKININ-1 (NK1) RECEPTOR ANTAGONISTS

CROSS-REFERENCE TO RELATED APPLICATION

This application claims the benefit of priority of U.S. Provisional Patent Application No. 61/791,217, filed Mar. 15, 2013, the contents of which being hereby incorporated by reference in its entirety for all purposes.

TECHNICAL FIELD

The invention relates to 3-piperidone compounds, and in particular, to (2S)-phenyl-3-piperidone and its synthesis method. Use of the thus-synthesized 3-piperidone compounds as potent neurokinin-1 (NK1) receptor antagonists is also provided.

BACKGROUND

Piperidones, such as 3-piperidone, and more specifically, (2S)-phenyl-3-piperidone, are important intermediates for a particularly useful class of therapeutic agents. From the core structure of the piperidone, various potent neurokinin-1 (NK1) receptor antagonists may be synthesized therefrom.

SUMMARY

Present invention is based on the inventors' surprising fording that biomass-derived furfural can be efficiently transformed into compounds having the 3-piperidone core structure which allows facile access to numerous neurokinin-1 (NK1) receptor antagonists. These potent NK1 receptor antagonists showed promising biological activities which may offer novel cures to disorders such as depression, anxiety and emesis. The advantages of present invention include the use of cheap and renewable biomass-derived starting material, shorter synthetic route with lesser purifications required and higher yield than existing methods.

Thus, in a first aspect of the invention, there is provided a method for synthesizing a compound of Formula (II)

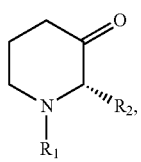

(II)

wherein
$R_1$ is a nitrogen-protecting group derivable from an amino group selected from the group consisting of tosylamide (Ts), t-butyl carbamate (Boc), benzyl carbamate (Cbz), 9-fluorenylmethyl carbamate (Fmoc), acetamide (Ac), trifluoroacetamide (TFA), benzylideneamine, triphenylmethylamine (Tritylamine), benzylamine (Bn), and phthalimide;
$R_2$ is selected from the group consisting of halogen, —C(O)—R, —NRR', —OR, —SR, —COOR, —CN, —NO$_2$, —C(O)—NRR', —NR'—C(O)—R, —SO$_2$—R, —(SO$_2$)—OR, linear or branched, substituted or unsubstituted C$_1$-C$_{10}$ alkyl; linear or branched, substituted or unsubstituted C$_2$-C$_{10}$ alkenyl; linear or branched, substituted or unsubstituted C$_2$-C$_{10}$ alkynyl; linear or branched, substituted or unsubstituted C$_1$-C$_{10}$ alkoxy; substituted or unsubstituted C$_3$-C$_{10}$ cycloalkyl; substituted or unsubstituted C$_3$-C$_{10}$ cycloalkenyl; substituted or unsubstituted C$_6$-C$_{10}$ aryl; substituted or unsubstituted C$_3$-C$_{10}$ heteroaryl;
R and R' are independently selected from the group consisting of H and linear or branched, substituted or unsubstituted C$_1$-C$_{10}$ alkyl.

The method includes:
reacting a compound of Formula (I)

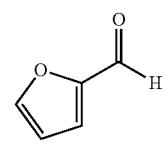

(I)

with NH$_2$R$_1$ to form a compound of Formula (IV)

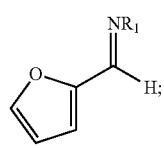

(IV)

reacting the compound of Formula (IV) with a precursor of R$_2$ in the presence of a rhodium catalyst to form an enantiomer of a compound of Formula (V)

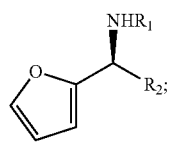

(V)

reacting the compound of Formula (V) with an oxidizing agent to form a compound of Formula (VI)

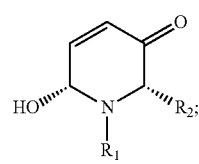

(VI)

reacting the compound of Formula (VI) with a reducing agent to form a compound of Formula (VII)

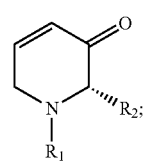

(VII)

and
hydrogenating the compound of Formula (VII) to form the compound of Formula (II).

In one embodiment, the compound of Formula (II) is

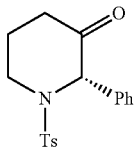 [SMILES: Cc1ccc(S(=O)(=O)N2CCCC(=O)[C@@H]2c2ccccc2)cc1]

(tosyl-protected (2S)-phenyl-3-piperidone).

In another aspect of the invention, use of the compound synthesized by the method of the first aspect as a neurokinin-1 (NK1) receptor antagonist is provided.

BRIEF DESCRIPTION OF THE DRAWINGS

In the drawings, like reference characters generally refer to the same parts throughout the different views. The drawings are not necessarily drawn to scale, emphasis instead generally being placed upon illustrating the principles of various embodiments. In the following description, various embodiments of the invention are described with reference to the following drawings.

DESCRIPTION

The following detailed description refers to the accompanying drawings that show, by way of illustration, specific details and embodiments in which the invention may be practised. These embodiments are described in sufficient detail to enable those skilled in the art to practise the invention. Other embodiments may be utilized and chemical changes may be made without departing from the scope of the invention. The various embodiments are not necessarily mutually exclusive, as some embodiments can be combined with one or more other embodiments to form new embodiments.

Figure 4:
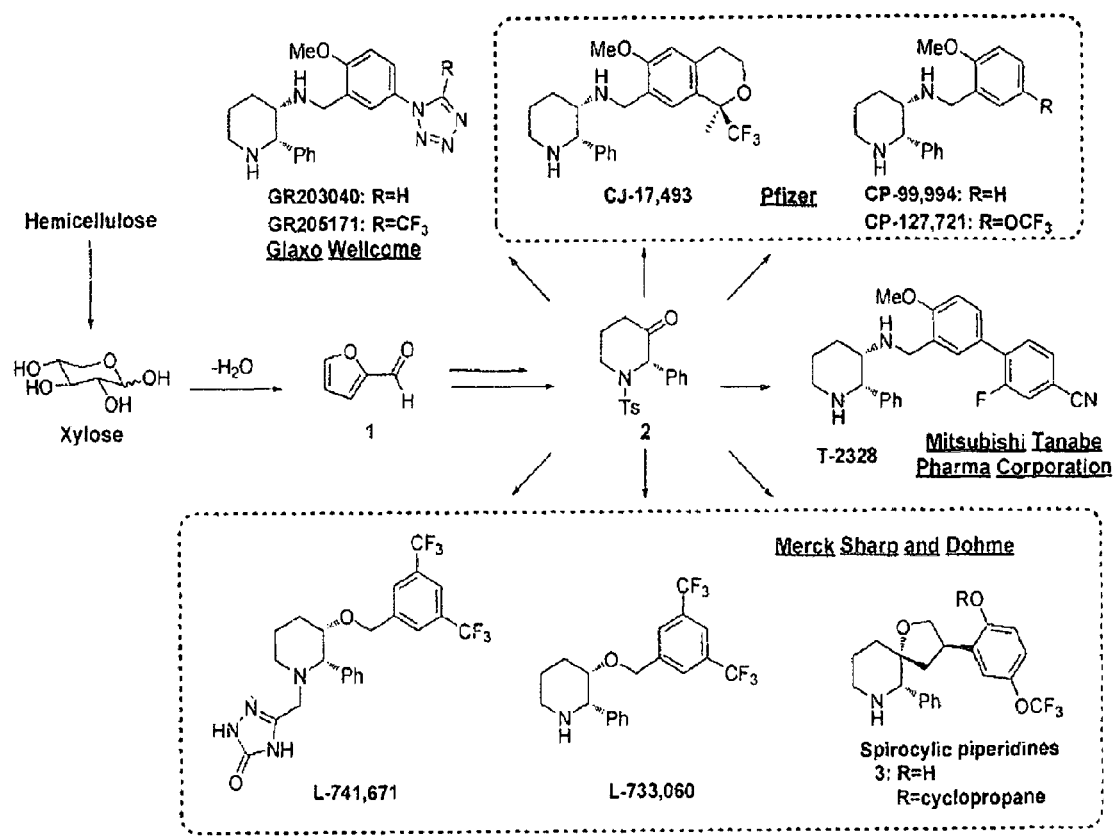
FIG. 4 shows a construction of piperidone core structure from furfural 1 to access various potent NK1 receptor antagonists.

With the depletion of fossil fuel resources, there is an increasing need to seek for a surrogate resource for both energy and chemical industry. Biomass is a promising feedstock for the chemical industry due to its renewability and the chemical diversity of its derivations. Furfural (i.e. a compound of Formula (I) defined below) is an example for a platform chemical derived from biomass and can provide an efficient synthetic route towards 3-piperidone core structure compounds, such as, but not limited to, tosyl-protected (2S)-phenyl-3-piperidone. Such 3-piperidone core structure compounds may be further reacted to gain access to various potent NK1 receptor antagonists (see FIG. 4).

In various embodiments, the synthesis method may involve a rhodium-catalyzed asymmetric arylation reaction and aza-Achmatowicz rearrangement with an overall yield of 57% over 5 steps and a recrystallization and a silica gel chromatography as purification. In later paragraphs, it will be described how tosyl-protected (2S)-phenyl-3-piperidone can allow facile access to various NK1 receptor antagonists and the synthetic utility of the 3-piperidone core structure was demonstrated with the synthesis of one such antagonist.

Thus, in a first aspect of the invention, there is provided a method for synthesizing a compound of Formula (II)

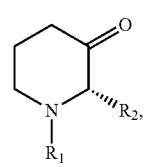

wherein
$R_1$ is a nitrogen-protecting group derivable from an amino group selected from the group consisting of tosylamide (Ts), t-butyl carbamate (Boc), benzyl carbamate (Cbz), 9-fluorenylmethyl carbamate (Fmoc), acetamide (Ac), trifluoroacetamide (TFA), benzylideneamine, triphenylmethylamine (Tritylamine), benzylamine (Bn), and phthalimide;
$R_2$ is selected from the group consisting of halogen, —C(O)—R, —NRR', —OR, —SR, —COOR, —CN, —NO$_2$, —C(O)—NRR', —SO$_2$—R, —(SO$_2$)—OR, linear or branched, substituted or unsubstituted $C_1$-$C_{10}$ alkyl; linear or branched, substituted or unsubstituted $C_2$-$C_{10}$ alkenyl; linear or branched, substituted or unsubstituted $C_2$-$C_{10}$ alkynyl; linear or branched, substituted or unsubstituted $C_2$-$C_{10}$ alkoxy; substituted or unsubstituted $C_3$-$C_{10}$ cycloalkyl; substituted or unsubstituted $C_3$-$C_{10}$ cycloalkenyl; substituted or unsubstituted $C_6$-$C_{10}$ aryl; substituted or unsubstituted $C_3$-$C_{10}$ heteroaryl;
R and R' are independently selected from the group consisting of H and linear or branched, substituted or unsubstituted $C_1$-$C_{10}$ alkyl.

The method includes:
reacting a compound of Formula (I)

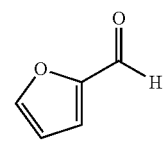

with NH$_2$R$_1$ to form a compound of Formula (IV)

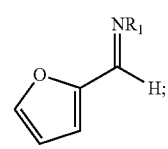

reacting the compound of Formula (IV) with a precursor of R$_2$ in the presence of a rhodium catalyst to form an enantiomer of a compound of Formula (V)

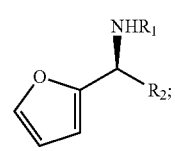

reacting the compound of Formula (V) with an oxidizing agent to form a compound of Formula (VI)

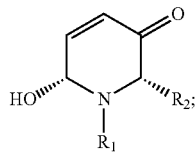
(VI)

reacting the compound of Formula (VI) with a reducing agent to form a compound of Formula (VII)

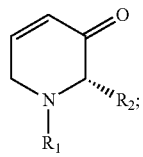
(VII)

and hydrogenating the compound of Formula (VII) to form the compound of Formula (II).

The term "aliphatic", alone or in combination, refers to a straight chain (i.e. linear) or branched chain hydrocarbon comprising at least one carbon atom. Aliphatics include alkyls, alkenyls, and alkynyls. In certain embodiments, aliphatics are optionally substituted, i.e. substituted or unsubstituted. The term "optionally substituted" or "substituted or unsubstituted" refers to a group in which none, one, or more than one of the hydrogen atoms have been replaced with one or more groups such as, but are not limited to, alkyl, heteroalkyl, haloalkyl, heteroholoalkyl, cycloalkyl, aryl, arylalkyl, heteroaryl, non-aromatic heterocycle, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups. In embodiments in which two or more hydrogen atoms have been substituted, the substituent groups may be linked to form a ring.

Aliphatics include, but are not limited to, methyl, ethyl, propyl, isopropyl, butyl, isobutyl, tert-butyl, pentyl, hexyl, ethenyl, propenyl, butenyl, ethynyl, butynyl, propynyl, and the like, each of which may be optionally substituted. As used herein, aliphatic is not intended to include cyclic groups.

The term "alkyl", alone or in combination, refers to a fully saturated aliphatic hydrocarbon. The alkyl may be linear or branched. In certain embodiments, alkyls are optionally substituted. In certain embodiments, an alkyl comprises 1 to 10 carbon atoms, for example 1 to 5 carbon atoms, wherein (whenever it appears herein in any of the definitions given below) a numerical range, such as "1 to 10" or "$C_1$-$C_{10}$", refers to each integer in the given range, e.g. "$C_1$-$C_{10}$ alkyl" means that an alkyl group comprising only 1 carbon atom, 2 carbon atoms, 3 carbon atoms, 4 carbon atoms, 5 carbon atoms, 6 carbon atoms, 7 carbon atoms, 8 carbon atoms, 9 carbon atoms, or 10 carbon atoms. Examples of alkyl groups include, but are not limited to, methyl, ethyl, n-propyl, isopropyl, n-butyl, isobutyl, sec-butyl, tert-butyl, tert-amyl, pentyl, hexyl, heptyl, octyl and the like.

The term "alkoxy", alone or in combination, refers to an aliphatic hydrocarbon having an alkyl-O— moiety. The alkoxy may be linear or branched. In certain embodiments, alkoxy groups are optionally substituted. In various embodiments, the alkoxy comprises 1 to 10 carbon atoms, i.e. $C_1$-$C_{10}$ alkoxy. Examples of alkoxy groups include, but are not limited to, methoxy, ethoxy, propoxy, butoxy and the like.

The term "alkenyl", alone or in combination, refers to an aliphatic hydrocarbon having one or more carbon-carbon double-bonds, such as two or three carbon-carbon double-bonds. The alkenyl may be linear or branched. In certain embodiments, alkenyls are optionally substituted, i.e. substituted or unsubstituted. In certain embodiments, an alkenyl comprises 2 to 10 carbon atoms. "$C_2$-$C_{10}$ alkenyl" means that an alkenyl group comprising only 2 carbon atoms, 3 carbon atoms, 4 carbon atoms, 5 carbon atoms, 6 carbon atoms, 7 carbon atoms, 8 carbon atoms, 9 carbon atoms, or 10 carbon atoms. Examples of alkenyls include, but are not limited to, ethenyl, propenyl, butenyl, 1,4-butadienyl, pentenyl, hexenyl, 4-methylhex-1-enyl, 4-ethyl-2-methylhex-1-enyl and the like.

The term "alkynyl", alone or in combination, refers to an aliphatic hydrocarbon having one or more carbon-carbon triple-bonds, such as two or three carbon-carbon triple-bonds. The alkynyl may be linear or branched. In certain embodiments, alkynyls are optionally substituted, i.e. substituted or unsubstituted. In certain embodiments, an alkynyl comprises 2 to 10 carbon atoms. "$C_2$-$C_{10}$ alkynyl" means that an alkynyl group comprising only 2 carbon atoms, 3 carbon atoms, 4 carbon atoms, 5 carbon atoms, 6 carbon atoms, 7 carbon atoms, 8 carbon atoms, 9 carbon atoms, or 10 carbon atoms. Examples of alkynyls include, but are not limited to, ethynyl, propynyl, butynyl, and the like.

The term "non-aromatic ring" refers to a group comprising a covalently closed ring that is not aromatic. The term "alicyclic" refers to a group comprising a non-aromatic ring wherein each of the atoms forming the ring is a carbon atom. Alicyclic groups may be formed by three, four, five, six, seven, eight, nine, or more than nine carbon atoms. In certain embodiments, alicyclics are optionally substituted, i.e. substituted or unsubstituted. In certain embodiments, an alicyclic comprises one or more unsaturated bonds, such as one or more carbon-carbon double-bonds. Alicyclics include cycloalkyls and cycloalkenyls. In various embodiments, $R_2$ may be a substituted or unsubstituted $C_3$-$C_{10}$ cycloalkyl. In further embodiments, $R_2$ may be a substituted or unsubstituted $C_3$-$C_{10}$ cycloalkenyl. Examples of alicyclics include, but are not limited to, cyclopropane, cyclobutane, cyclopentane, cyclopentene, cyclopentadiene, cyclohexane, cyclohexene, 1,3-cyclohexadiene, 1,4-cyclohexadiene, cycloheptane, and cycloheptene.

The term "aryl" refers to an aromatic ring wherein each of the atoms forming the ring is a carbon atom. Aryl rings may be formed by five, six, seven, eight, nine, or more than nine carbon atoms. Aryl groups may be optionally substituted. In various embodiments, $R_2$ may be a substituted or unsubstituted $C_6$-$C_{10}$ aryl.

The term "heteroaryl" refers to an aromatic heterocycle. Heteroaryl rings may be formed by three, four, five, six, seven, eight, nine, or more than nine atoms. Heteroaryls may be optionally substituted. Examples of heteroaryl groups include, but are not limited to, aromatic C3-8 heterocyclic groups comprising one oxygen or sulfur atom or up to four nitrogen atoms, or a combination of one oxygen or sulfur atom and up to two nitrogen atoms, and their substituted as well as benzo- and pyrido-fused derivatives, for example, connected via one of the ring-forming carbon atoms. In certain embodiments, heteroaryl groups are optionally substituted with one or more substituents, independently selected from halo, hydroxy, amino, cyano, nitro, alkylamido, acyl, C1-6-alkoxy, C1-6-alkyl, C1-6-hydroxyalkyl, C1-6-aminoallcyl, alkylamino, alkylsulfenyl, alkylsulfinyl, alkylsulfonyl, sulfamoyl, or trifluoromethyl. Examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quinoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline, and quinoxaline. In some embodiments, the substituents are halo, hydroxy, cyano, O—C1-6-alkyl, C1-6-alkyl, hydroxy-C1-6-alkyl, and amino-C1-6-alkyl. In various embodiments, $R_2$ may be a substituted or unsubstituted $C_3$-$C_{10}$ heteroaryl.

A "halo" or "halogen" group refers to fluorine, chlorine, bromine or iodine.

In various embodiments, $R_2$ may be selected from the group consisting of linear or branched, substituted or unsubstituted $C_1$-$C_{10}$ alkyl, and substituted or unsubstituted $C_6$-$C_{10}$ aryl.

In further embodiments, $R_2$ may be a substituted or unsubstituted $C_6$-$C_{10}$ aryl.

In yet further embodiments, $R_2$ may be a substituted or unsubstituted phenyl.

In one embodiment, $R_2$ may be an unsubstituted phenyl.

In embodiments where $R_2$ is unsubstituted phenyl, the compound of Formula (IV) may be reacted with triphenylcyclotriboroxane ((PhBO)$_3$) in the presence of a rhodium catalyst to form an enantiomer of a compound of Formula (V). In such embodiments, the rhodium catalyst may be chlorobis(ethylene)rhodium(1) dimer ([RhCl($C_2H_4$)]$_2$). Alternatively, $R_2$ may be any one of the following:

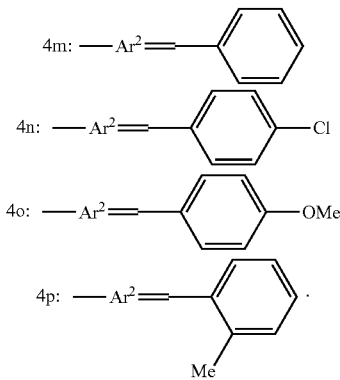

$R_1$ is a nitrogen-protecting group derivable from an amino group defined above.

In certain embodiments, $R_1$ may be a nitrogen-protecting group derivable from an amino group selected from the group consisting of Ts, Boc, Bn.

In one embodiment, $R_1$ may be a nitrogen-protecting group derivable from tosylamide or alternatively known as p-toluenesulfonamide.

In embodiments where $R_1$ is a nitrogen-protecting group derivable from tosylamide, the compound of Formula (I) may be reacted with tosylamide in presence of a Lewis acid to form the compound of Formula (IV).

In one embodiment where $R_1$ is a nitrogen-protecting group derivable from tosylamide, the compound of Formula (I) may be reacted with tosylamide in presence of boron trifluoride diethyl etherate (BF$_3$.O(Et)$_2$) or para-toluenesulfonic acid (PTSA) to form the compound of Formula (IV).

In various embodiments, the compound of Formula (V) may be reacted with an oxidizing agent comprising N-bromosuccinimide (NBS), meta-chloroperoxybenzoic acid (MCPBA), bromine in methanol, or titanium isopropoxide (Ti(OiPr4)) with tert-butyl hydroperoxide (TBPH) to form a compound of Formula (VI).

In various embodiments, the compound of Formula (VI) may be reacted with a reducing agent comprising triethylsilane (Et$_3$SiH), dimethylethylsilane, dimethylphenylsilane, dimethylbenzylsilane, or diethyoxymethylsilane to form a compound of Formula (VII).

In various embodiments, the compound of Formula (VII) may be hydrogenated by hydrogen to form the compound of Formula (H).

In further embodiments, the compound of Formula (VII) may be hydrogenated by hydrogen in presence of a palladium activated on carbon (Pd/C) catalyst to form the compound of Formula (II).

In one embodiment, the compound of Formula (II) is

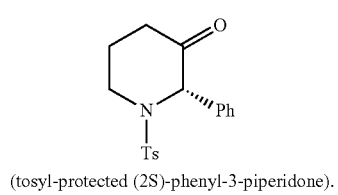 [SMILES: Cc1ccc(S(=O)(=O)N2CCCC(=O)[C@@H]2c2ccccc2)cc1]

(tosyl-protected (2S)-phenyl-3-piperidone).

Figure 1:
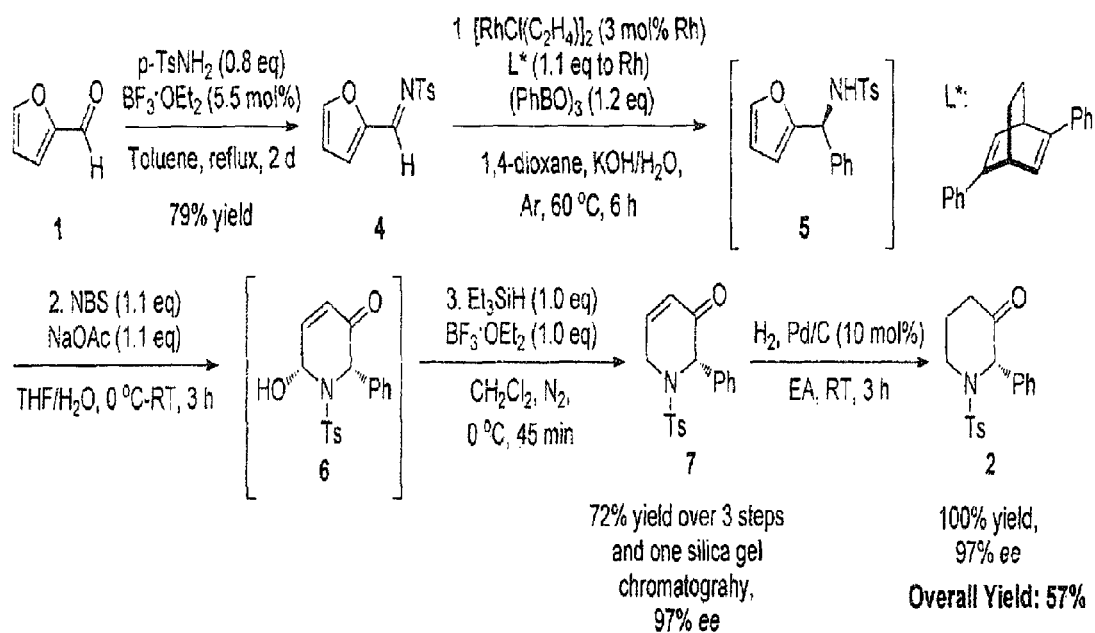
FIG. 1 shows the synthesis of tosyl-protected (2S)-phenyl-3-piperidone 2 from biomass-derived furfural 1.

For the purposes of brevity and illustration, preferred embodiments of the present invention are described with reference to FIG. 1, which shows the synthesis of tosyl-protected (2S)-phenyl-3-piperidone 2 from biomass-derived furfural 1.

Figure 2:
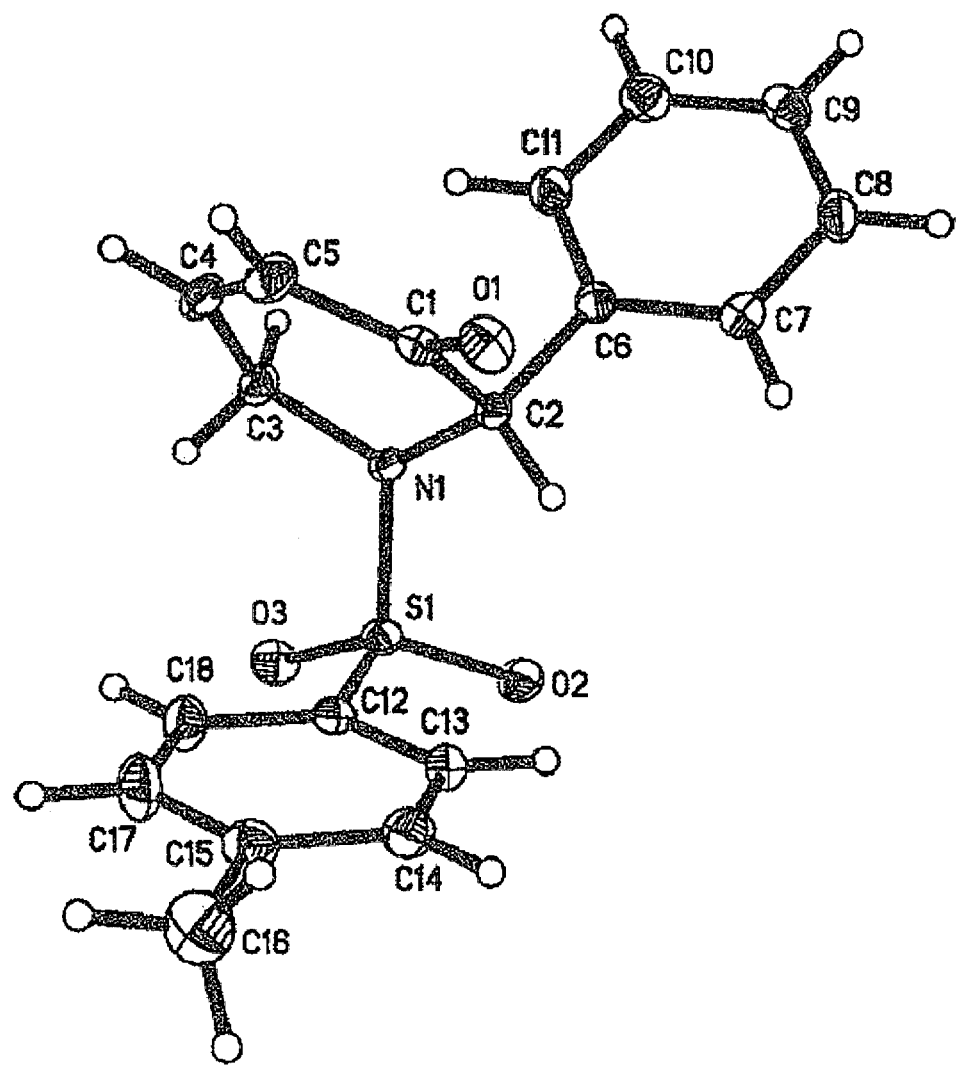
FIG. 2 shows the single-crystal X-ray crystallography of the direct precursor (VII) of 2.

In a first step, furfural 1 is reacted to form imine 4 in the presence of 4-methylbenzenesulfonamide and a lewis acid catalyst with a good yield of 79% over 2 recrystallizations. Imine 4 was then subjected to an enantioselective rhodium-catalyzed asymmetric arylation methodology developed by Hayashi's group (Tokunaga, N.; Otomaru, Y.; Okamoto, K.; Ueyama, K.; Shintani, R.; Hayashi, T. *J. Am. Chem. Soc.* 2004, 126, 13584-13585) to afford furylamine 5 with 97% yield and 99% enantiomeric excess (ee) after column chromatography. In view of the efficiency of this step, subsequent reactions were not subjected to chromatographic purification and crude 5 underwent the aza-Achmatowicz rearrangement (Achmatowicz Jr, O.; Bukowski, P.; Szechner, B.; Zwierzchowska, Z.; Zamojski, A. *Tetrahedron* 1971, 27, 1973-1996) with N-bromosuccinimide (NBS) as oxidant to yield hemiaminal 6. Crude 6 was able to be immediately reduced ((a) Kursanov, D. N.; Parnes, Z. N.; Loim, N. M. Synthesis 1974, 633-651; (b) Lewis, M. D.; Ow, J. K.; Kishi, Y. *J. Am. Chem. Soc.* 1982, 104, 4976) without further purification to give 7 with 72% yield and 97% ee over 3 steps from 4. The absolute configuration of 7 is verified using single-crystal X-ray crystallography (see FIG. 2) and recrystallization of 7 from ethanol or Hexane/Ethyl Acetate can increase the ee to above 99% to obtain the enantiomerically pure 7. The slight loss in ee was determined to be due to the slight acidity of silica gel. Hence, ee loss of 7 can be minimized by performing flash silica gel chromatography to yield 7 in 97% ee. 7 was then hydrogenated using Pd/C in a quantitative conversion to yield tosyl-protected (2S)-phenyl-3-piperidone 2. Thus, key intermediate 2 was efficiently synthesized from biomass-derived furfural 1, in an overall yield of 57% over 5 steps.

Figure 3:
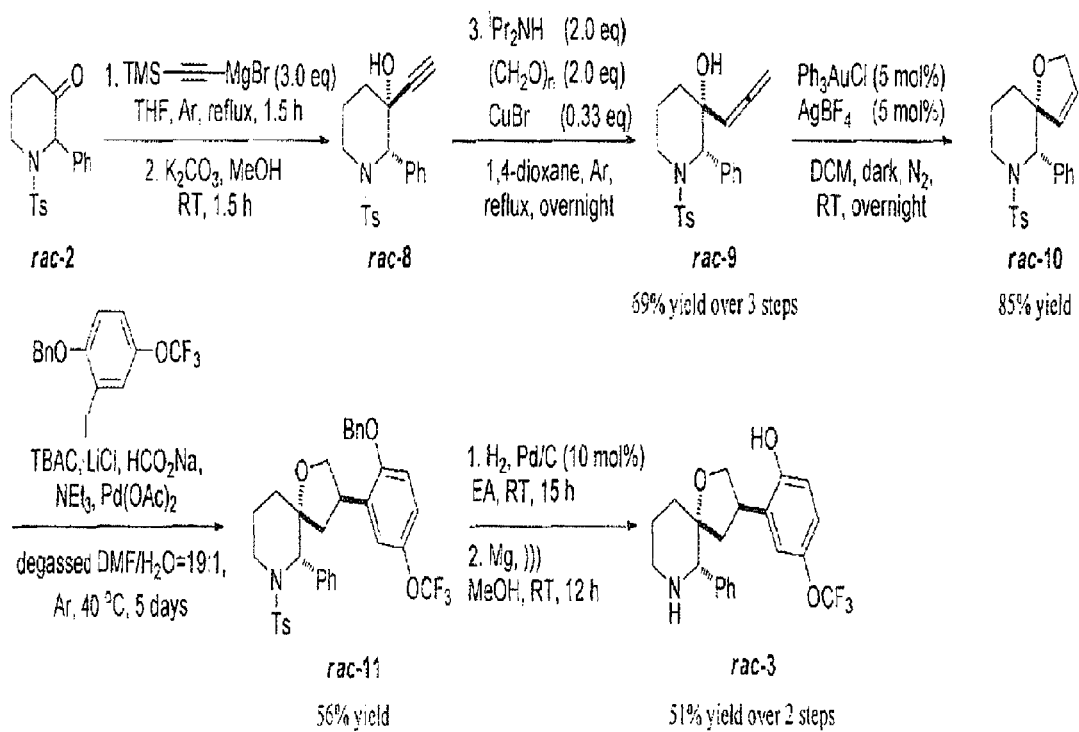
FIG. 3 shows the synthesis of rac-3 using Searles-Crabbe Homologation, Au-catalyzed cyclo isomerisation and reductive Heck reaction.

FIG. 3 is to illustrate use of tosyl-protected (2S)-phenyl-3-piperidone 2 to synthesize NK1 receptor antagonist 3. rac-2 was able to undergo a Grignard reaction and then subsequent TMS deprotection to form rac-8 which was immediately subjected to Searles-Crabbe Homologation (Searles, S.; Li, Y.; Nassim, B.; Lopes, M.-T. R.; Iran, P. T.; Crabbe, P. *J. Chem. Soc. Perkin Trans.* 1 1984, 747-751) conditions without further purification to transform the alkyne moiety to an allene rac-9 in 69% yield over 3 steps. Au-catalyzed cycloisomerisation (Gockel, B.; Krause, N. *Org. Lett.* 2006, 8, 4485-4488) of rac-9 constructed the spirocycle rac-10 in 85% yield and while a regio- and stereo-selective reductive Heck reaction developed by Merck ((a) Wallace, D. J.; Goodman, J. M.; Kennedy, D. J.; Davies, A. J.; Cowden, C. J.; Ashwood, M. S.; Cottrell, I. F.; Dolling, U.-H.; Reider, P. J. *Org. Lett.* 2001, 3, 671-674; (b) Kulagowski, J. J.; Curtis, N. R.; Swain, C. J.; Williams, B. J. *Org. Lett.* 2001, 3, 667-670) transformed rac-10 to rac-11 in 56% yield. The relative stereochemistry of rac-11 was also confirmed using NOE analysis where the two benzylic protons in rac-11 were shown to have NOE interactions, in agreement with the results reported by Merck. rac-11 was finally subjected to Pd-catalyzed hydrogenation and Mg-promoted tosyl deprotection with the help of sonication in 51% yield over 2 steps to complete the synthesis of rac-3 as a white solid instead of a pale yellow oil reported by Merck (Wallace, D. J.; Goodman, J. M.; Kennedy, D. J.; Davies, A. J.; Cowden, C. J.; Ashwood, M. S.; Cottrell, I. F.; Dolling, U.-H.; Reider, P. J. *Org. Lett.* 2001, 3, 671-674) for the reported enantiopure form.

In summary, it has been demonstrated the efficiency of synthesizing tosyl-protected (2S)-phenyl-3-piperidone 2 from biomass-derived furfural 1 by employing Hayashi's rhodium-catalyzed asymmetric arylation methodology as well as the aza-Achmatowicz rearrangement reaction to achieve 2 in 57% yield and 97% ee over only 5 steps. This synthesis strategy has the advantage of a shorter route, less purification, higher yield and originates from a renewable source, thus improving its sustainability as compared to existing methods. It may also be employed across various different substituents and nitrogen protecting groups to synthesize a variety of protected 2-substituted-3-piperidones. Most importantly, 2 allows facile access to numerous biologically active compounds and its synthetic usefulness has been further demonstrated with the synthesis of rac-3.

By "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

By "about" in relation to a given numerical value, such as for temperature and period of time, it is meant to include numerical values within 10% of the specified value.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

In order that the invention may be readily understood and put into practical effect, particular embodiments will now be described by way of the following non-limiting examples.

EXAMPLES

General Methods

All reagents were commercially purchased and were used as received for the reactions. All reactions were carried out in oven-dried glassware while THF was freshly distilled from Na/Benzophenone ketyl and DCM was freshly distilled from Calcium Hydride. Thin-layer chromatography (TLC) was conducted with Merck 60 F254 precoated silica gel plate (0.2 mm thickness) and visualized under UV, by potassium permanganate or ceric ammonium molybdate stain. Flash chromatography was performed using Merck silica gel 60 with distilled solvents. $^1$H-NMR spectra were performed on a Bruker Avance 300, Bruker Avance 400 or Bruker Avance 500 NMR spectrometer and are reported in ppm downfield from $SiMe_4$ ($\delta$ 0.0), relative to the signal of chloroform-d ($\delta$=7.26, singlet) or methanol-$d_4$ ($\delta$=3.31, quintet). Data reported as: s=singlet, d=doublet, t=triplet, q=quartet, m=multiplet, b=broad; coupling constant(s) in Hz; integration. Proton-decoupled $^{13}$C-NMR spectra were recorded on Bruker Avance 300 (75 MHz) or 400 (100 MHz) or 500 (125 MHz) spectrometer and are reported in ppm using solvent as an internal standard ($CDCl_3$ at 77.16 ppm, CD3OD at 49.15 ppm). IR spectra were recorded using nujol mull technique on NaCl plates on a Shimadzu IRPrestige-21 FT-IR Spectrophotometer or under attenuated total reflection (AIR) conditions on a PerkinElmer Spectrum 100 FT-IR Spectrometer and were reported in frequency of absorption (cm$^{-1}$). High-resolution mass spectral analysis (HRMS) was performed on Q-T of Premier mass spectrometer (Waters Corporation).

Synthesis and Characterization of Compounds

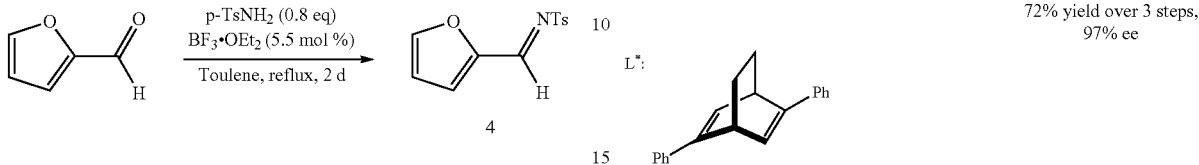

N-(furan-2-ylmethylene)-4-methylbenzenesulfonamide (4)

Furfural (14.0 g, 146 mmol, 1.0 eq), 4-methylbenzenesulfonamide (20.0 g, 117 mmol, 0.8 eq), boron trifluoride etherate (1.0 mL, 1.15 g, 8.1 mmol, 5.5 mol %) and toluene (150 mL) were added into a round-bottom flask fitted with a Dean Stark Trap. The mixture was heated at reflux for 2 days and activated charcoal was added and stirred for 1 h. The mixture was filtered and the filtrate concentrated under reduced pressure to give a brown solid. Recrystallization from benzene gave N-(furan-2-ylmethylene)-4-methylbenzenesulfonamide 4 as brown crystals (22.9 g, 91.9 mmol, 79%).

Yield=79%. $R_f$=0.32 (Hexane/Ethyl Acetate=2:1). Melting point=100-101° C. (Reported value in Harris, J. M.; Padwa, A. *Org. Lett.* 2002, 4, 2029-2031=100-101° C.)

$^1$H-NMR (300 MHz, CDCl$_3$) δ (ppm): 8.81 (s, 1H), 7.87 (d, J=8.3 Hz, 2H), 7.74 (d, J=1.6 Hz, 1H), 7.34-7.31 (m, 3H), 6.65 (dd, J=3.6 Hz, 1.7 Hz, 1H), 2.43 (s, 3H).

$^{13}$C-NMR (100 MHz, CDCl$_3$) δ (ppm): 155.7, 149.8, 149.1, 144.6, 135.2, 129.8, 128.1, 124.7, 113.7, 21.7.

FTIR (Nujol, NaCl, cm$^{-1}$): 1607, 1315, 1155, 932.

HRMS (ESI) m/z Calcd for C$_{12}$H$_{12}$NO$_3$S [M+H]$^+$: 250.0538. Found: 250.0541.

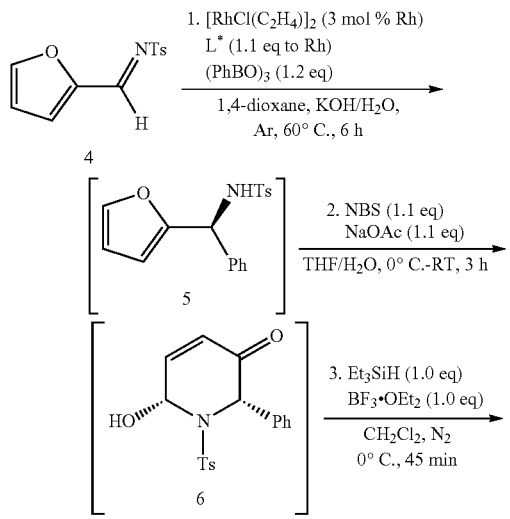

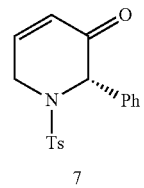

7

72% yield over 3 steps, 97% ee

L*:

(S)—N-(furan-2-yl(phenyl)methyl)-4-methylbenzenesulfonamide (5)

To the solution of [RhCl(C$_2$H$_4$)$_2$]$_2$ (5.8 mg, 0.015 mmol, 3 mol % Rh) and (R,R)-Ph-bod* (8.5 mg, 0.033 mmol, 1.1 eq to Rh) in anhydrous 1,4-dioxane (2.5 mL) was added aqueous KOH (65.0 μL, 3.1 M, 20 mol % KOH, H$_2$O: 1 eq to boron) at room temperature and stirred for 15 min. This solution containing the catalyst was added to the solution of imine 4 (249 mg, 1.0 mmol, 1.0 eq) and 2,4,6-triphenylboroxine (374 mg, 1.2 mmol, 1.2 eq) in anhydrous 1,4-dioxane (4.0 mL) at the same temperature. After 6 h stirring at 60° C., the mixture was passed through a short silica gel column (pre-treated with methanol, eluent: ethyl acetate) to give 5 as the crude product and was immediately subjected to the next step without any further purification.

Data for 5 after purification using silica gel chromatography (Eluent: Hexane/Ethyl Acetate=5:1) to give (S)—N-(furan-2-yl(phenyl)methyl)-4-methylbenzenesulfonamide 5 as a pale yellow solid in 97% yield, ee≈99%. The ee was determined on Chiralcel OD-H column with hexane/2-propanol=90:10, flow=0.5 mL/min, wavelength=220 nm. Retention times: 20.5 min [(S)-enantiomer], 22.0 min [(R)-enantiomer].

Yield=97%. ee≈99%. $[α]^{22}_D$=−18.1 (c=1.03, CHCl$_3$) for 99% ee. (Tokunaga, N.; Otomaru, Y.; Okamoto, K.; Ueyama, K.; Shintani, R.; Hayashi, T. *J. Am. Chem. Soc.* 2004, 126, 13584-13585: $[α]^{20}_D$=−21.6 (c=1.03, CHCl$_3$) for 99% ee.)

$R_f$=0.53 (Hexane/Ethyl Acetate=2:1). Melting point=129-130° C. (Reported value for rac-5 in Koulocheri, S. D.; Haroutounian, S. A.; Apostolopoulos, C. D.; Chada, R. K.; Couladouros, E. A. *Eur. J. Org. Chem.* 1999, 1999, 1449-1453.=132-133° C.)

$^1$H-NMR (300 MHz, CDCl$_3$) δ (ppm): 7.58 (d, J=8.3 Hz, 2H), 7.26-7.22 (m, 4H), 7.19-7.14 (m, 4H), 6.19 (dd, J=3.2 Hz, 1.9 Hz, 1H), 5.99 (d, J=3.2 Hz, 1H), 5.61 (d, J=7.7 Hz, 1H), 5.23 (d, J=7.6 Hz, 1H), 2.38 (s, 3H).

$^{13}$C-NMR (125 MHz, CDCl$_3$) δ (ppm): 152.3, 143.3, 142.7, 138.4, 137.5, 129.5, 128.7, 128.1, 127.3, 127.2, 110.3, 108.5, 55.6, 21.6.

FTIR (Nujol, NaCl, cm$^{-1}$): 3265, 1597, 1319, 1159, 928.

HRMS (ESI) m/z Calcd for C$_{18}$H$_{18}$NO$_3$S [M+H]$^+$: 328.1007. Found: 328.0992.

Crude 5 from the previous step was dissolved in a mixture of THF (10.0 mL) and H$_2$O (3.3 mL) at 0° C. Sodium acetate (90 mg, 1.1 mmol, 1.1 eq) was added before N-bromosuccinimide (196 mg, 1.1 mmol, 1.1 eq) was slowly added in portions at 0° C. over 15 min. The mixture was stirred for 3 h at room temperature after the addition of N-bromosuccinimide before solid Na₂S₂O₃ and brine (7 mL) was added. The mixture was extracted with ethyl acetate (3×20 mL) and the combined organic layers were washed with brine (25 mL), dried over anhydrous magnesium sulphate, filtered and concentrated under reduced pressure to give 6 as the crude product and 6 was immediately subjected to the next step without any further purification.

Data for rac-6 (recrystallized in CH₂Cl₂ from crude product as pale yellow crystals):

$R_f$=0.26 (Hexane/Ethyl Acetate=2:1). Melting point=122-123° C. (Decomposed)

¹H-NMR (300 MHz, CDCl₃) δ (ppm): 7.64 (d, J=8.3 Hz, 2H), 7.56-7.53 (m, 2H), 7.33-7.24 (m, 5H), 6.86 (dd, J=10.4 Hz, 4.1 Hz, 1H), 6.11 (dd, J=10.4 Hz, 1.4 Hz, 1H), 5.99-5.96 (m, 1H), 5.47 (s, 1H), 3.48-3.46 (m, 1H), 2.40 (s, 3H).

¹³C-NMR (125 MHz, CDCl₃) δ (ppm): 191.2, 144.6, 143.7, 136.8, 136.3, 130.3, 128.8, 128.4, 127.8, 127.6, 127.0, 73.6, 64.2, 21.7.

FTIR (Nujol, NaCl, cm⁻¹): 3480, 1682, 1649, 1597, 1321, 1155.

HRMS (ESI) m/z Calcd for $C_{18}H_{18}NO_4S$ [M+H]⁺: 344.0957. Found: 344.0970.

(S)-2-phenyl-1-tosyl-1,6-dihydropyridin-3(2H)-one (7)

The crude rearrangement product 6 was dissolved in anhydrous CH₂Cl₂ (9.0 mL) and cooled down to 0° C. under N₂ protection. Triethylsilane (159 μL, 116 mg, 1.0 mmol, 1.0 eq) was added followed by boron trifluoride etherate (123 μL, 142 mg, 1.0 mmol, 1.0 eq) and the mixture was allowed to stirred at 0° C. for 45 min before H₂O (10 mL) was added to quench the reaction. The mixture was extracted with CH₂Cl₂ (3×20 mL). The combined organic layers were washed with brine (25 mL), dried over anhydrous magnesium sulphate and filtered. Concentration under reduced pressure and purification using silica gel chromatography (Eluent: Hexane/Ethyl acetate 4:1) gave (S)-2-phenyl-1-tosyl-1,6-dihydropyridin-3(2H)-one 7 as a brown solid (234 mg, 0.72 mmol, 72% over 3 steps), ee=97%. The ee was determined on Chiralcel OD-H column with hexane/2-propanol=90:10, flow=0.5 mL/min, wavelength=220 nm. Retention times: 29.7 min [(R)-enantiomer], 34.0 min [(S)-enantiomer].

Yield 72% over 3 steps. ee=97% over 3 steps. $[α]^{21}_D$=+123 (c 1.32, CH₂Cl₂) for 97% ee. (Gaucher, X.; Jida, M.; Ollivier, J. Synlett 2009, 3320-3322. $[α]^{20}_D$=−145 (c=0.3, CH₂Cl₂))

$R_f$=0.42 (Hexane/Ethyl Acetate=2:1). Melting point=131-132° C. (Reported as a yellow oil in Gaucher, X.; Jida, M.; Ollivier, J. Synlett 2009, 3320-3322.)

¹H-NMR (500 MHz, CDCl₃) δ (ppm): 7.62 (d, J=8.3 Hz, 2H), 7.35-7.29 (m, 5H), 7.25 (d, J=8.0 Hz, 2H), 6.69 (ddd, J=10.4 Hz, 4.9 Hz, 1.9 Hz, 1H), 5.94 (ddd, J=10.4 Hz, 2.4 Hz, 1.6 Hz, 1H), 5.62 (s, 1H), 4.46 (ddd, J=20.9 Hz, 4.8 Hz, 1.4 Hz, 1H), 3.84 (dt, J=20.9 Hz, 2.4 Hz, 1.6 Hz, 1H), 2.40 (s, 3H).

¹³C-NMR (125 MHz, CDCl₃) δ (ppm): 192.3, 144.6, 144.2, 136.5, 133.2, 130.1, 129.1, 128.7, 127.2, 127.0, 64.1, 41.8, 21.7.

FTIR (Nujol, NaCl, cm⁻¹): 1688, 1628, 1597, 1341, 1159.

HRMS (ESI) m/z Calcd for $C_{18}H_{18}NO_3S$ [M+H]⁺: 328.1007. Found: 328.1020.

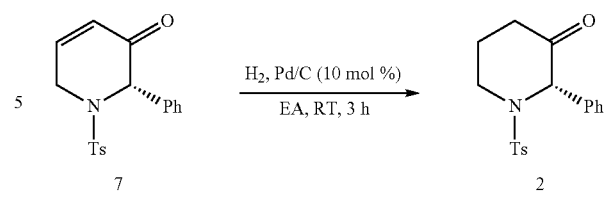

(S)-2-phenyl-1-tosylpiperidin-3-one (2)

(S)-2-phenyl-1-tosyl-1,6-dihydropyridin-3(2H)-one 7 (151 mg, 0.462 mmol, 1.0 eq) was dissolved in ethyl acetate (10 mL) and palladium on activated charcoal (10 wt %, 49 mg, 0.046 mmol, 10 mol %) was added. The round bottom flask was evacuated and refilled with H₂ thrice using a H₂ balloon. The reaction was stirred for 3 h at room temperature before being filtered through a pad of celite. Concentration under reduced pressure gave (S)-2-phenyl-1-tosylpiperidin-3-one 2 as a pale yellow solid (152 mg, 0.462 mmol, 100%), ee=97%. The ee was determined on Chiralcel OD-H column with hexane/2-propanol=90:10, flow=0.5 mL/min, wavelength=220 nm. Retention times: 19.7 min [(R)-enantiomer], 23.0 min [(S)-enantiomer].

Yield=100%. ee=97%. $[α]^{23}_D$=−10.0 (c=1.01, CH₂Cl₂) for 97% ee. (Gaucher, X.; Jida, M.; Ollivier, J. Synlett 2009, 3320-3322. $[α]^{20}_D$=+5 (c=0.2, CH₂Cl₂)).

$R_f$=0.50 (Hexane/Ethyl Acetate=2:1). Melting point=152-153° C. (Reported in Gaucher, X.; Jida, M.; Ollivier, J. Synlett 2009, 3320-3322. as deliquescent solid and reported value in Kokotos, C. G.; Aggarwal, V. K. Chem. Commun. 2006, 2156-2158.=152-154° C.)

¹H-NMR (300 MHz, CDCl₃) δ (ppm): 7.71 (d, J=8.3 Hz, 2H), 7.36-7.26 (m, 7H), 5.57 (s, 1H), 3.86 (dt, J=14.0 Hz, 5.0 Hz, 1H), 3.44 (ddd, J=14.0 Hz, 9.6 Hz, 4.3 Hz, 1H), 2.43 (s, 3H), 2.40-2.31 (m, 1H), 2.17 (dt, J=16.0 Hz, 5.3 Hz, 1H), 1.79-1.61 (m, 2H).

¹³C-NMR (125 MHz, CDCl₃) δ (ppm): 204.6, 144.0, 137.3, 134.0, 130.1, 129.3, 128.3, 127.2, 125.9, 66.9, 41.3, 36.9, 23.6, 21.7.

FTIR (Nujol, NaCl, cm⁻¹): 1721, 1595, 1342, 1157.

HRMS (ESI) m/z Calcd for $C_{18}H_{20}NO_3S$ [M+H]⁺: 330.1164. Found: 330.1166.

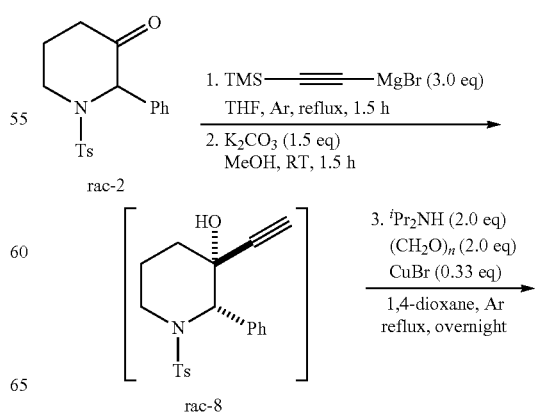

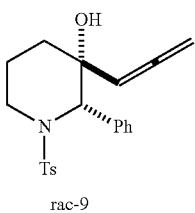

rac-9 rac-3-ethynyl-2-phenyl-1-tosylpiperidin-3-ol (rac-8)

An oven-dried 50 mL two-neck round bottom flask equipped with a stir bar and a reflux condenser was cooled under vacuum and back-filled with Ar thrice before being charged with methylmagnesium bromide (2.0 mL of a 3.0 M solution in ether, 6.0 mmol, 3.0 eq), anhydrous THF (2.7 mL) and trimethylsilylacetylene (1.3 mL, 882 mg, 9.0 mmol, 4.5 eq). The mixture was heated at reflux for 1.5 h before rac-2 (658 mg, 2.0 mmol, 1.0 eq) in anhydrous THF (16.0 mL) was added and the mixture was allowed to stir at reflux for 1.5 h before saturated aqueous $NH_4Cl$ solution (10 mL) was added to quench the reaction. The layers were separated and the aqueous phase extracted with ethyl acetate (3×15 mL). The combined organic extracts were washed with saturated aqueous $NaHCO_3$ solution (30 mL), brine (30 mL), dried over anhydrous magnesium sulphate and filtered. Concentration under reduced pressure gave the crude product which was used immediately in the next step without further purification.

The crude product from the Grignard reaction was dissolved in MeOH (20 mL) and solid $K_2CO_3$ (414 mg, 3.0 mmol, 1.5 eq) was added and the mixture was allowed to stir at room temperature for 1.5 h. The solvent was removed under reduced pressure and saturated aqueous $NH_4Cl$ solution (10 mL) and EA (20 mL) were added and the layers were separated. The aqueous phase was extracted with ethyl acetate (3×10 mL). The combined organic extracts were washed with saturated aqueous $NaHCO_3$ solution (20 mL), brine (20 mL), dried over anhydrous magnesium sulphate and filtered. Concentration under reduced pressure gave rac-8 as the crude product which was used immediately in the next step without further purification.

Data for rac-8 after purification using silica gel chromatography (Eluent: Hexane/Ethyl Acetate=2:1) to give rac-3-ethynyl-2-phenyl-1-tosylpiperidin-3-ol rac-8 as a white solid.

$R_f$=0.34 (Hexane/Ethyl Acetate=2:1). Melting point=169-170° C.

$^1$H-NMR (300 MHz, $CDCl_3$) δ (ppm): 7.41 (d, J=8.3 Hz, 2H), 7.34-7.32 (m, 2H), 7.26-7.22 (m, 3H), 7.06 (d, J=8.1 Hz, 2H), 5.31 (s, 1H), 3.82 (dd, J=13.8 Hz, 4.1 Hz, 1H), 3.39-3.29 (m, 1H), 2.53 (s, 1H), 2.34 (s, 3H), 2.02-1.98 (m, 2H), 1.94 (s, 1H), 1.87-1.83 (m, 2H).

$^{13}$C-NMR (75 MHz, $CDCl_3$) δ (ppm): 143.0, 136.9, 136.2, 129.7, 129.2, 128.4, 128.3, 127.4, 86.1, 73.6, 69.0, 65.6, 41.2, 32.5, 22.0, 21.6.

FTIR (AIR, $cm^{-1}$): 3469, 3297, 3067, 3032, 1597, 1324, 1161.

HRMS (ESI) m/z Calcd for $C_{20}H_{22}NO_3S$ $[M+H]^+$: 356.1320. Found: 356.1311.

rac-2-phenyl-3-(propa-1,2-dien-1-yl)-1-tosylpiperidin-3-ol (rac-9)

Isopropylamine (560 µL, 404 mg, 4.0 mmol, 2.0 eq) was added to a suspension of crude rac-8, paraformaldehyde (120 mg, 4.0 mmol, 2.0 eq) and CuBr (95 mg, 0.67 mg, 33 mol %) in anhydrous 1,4-dioxane (16.0 mL). The reaction was refluxed overnight and then cooled to room temperature before being filtered through a pad of celite. Concentration under reduced pressure and purification using silica gel chromatography (Eluent: Hexane/Ethyl Acetate=5:1) gave rac-2-phenyl-3-(propa-1,2-dien-1-yl)-1-tosylpiperidin-3-ol rac-9 as a yellow solid (510 mg, 1.38 mmol, 69%) over 3 steps.

Yield=69% over 3 steps. $R_f$=0.38 (Hexane/Ethyl Acetate=2:1). Melting point=96-97° C.

$^1$H-NMR (400 MHz, $CDCl_3$) δ (ppm): 7.30 (d, J=8.2 Hz, 2H), 7.25-7.16 (m, 5H), 7.02 (d, J=8.0 Hz, 2H), 5.52 (t, J=6.7 Hz, 1H), 5.01 (s, 1H), 4.99-4.92 (m, 2H), 3.80 (dd, J=13.1 Hz, 4.5 Hz, 1H), 3.38 (td, J=12.1 Hz, 4.3 Hz, 1H), 2.32 (s, 3H), 1.97-1.91 (m, 2H), 1.82-1.79 (m, 1H), 1.73-1.67 (m, 1H), 1.63 (s, 1H).

$^{13}$C-NMR (100 MHz, $CDCl_3$) δ (ppm): 206.7, 142.8, 136.8, 129.7, 129.2, 128.2×2, 128.0, 127.2, 98.1, 80.1, 71.3, 65.6, 41.2, 32.1, 21.5×2.

FTIR (Nujol, NaCl, $cm^{-1}$): 3532, 1960, 1597, 1329, 1153.

HRMS (ESI) m/z Calcd for $C_{21}H_{24}NO_3S$ $[M+H]^+$: 370.1477. Found: 370.1461.

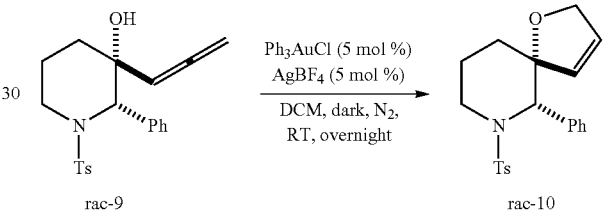

rac-9     rac-10 rac-6-phenyl-7-tosyl-1-oxa-7-azaspiro[4.5]dec-3-ene (rac-10)

α-allenic alcohol rac-9 (200 mg, 0.54 mmol, 1.0 eq), chloro(triphenylphosphine)gold (I) (13 mg, 0.027 mmol, 5 mol %) and silver tetrafluoroborate (5 mg, 0.027 mmol, 5 mol %) were dissolved in anhydrous $CH_2Cl_2$ (2.0 mL) under $N_2$ and in the dark. The mixture was allowed to stir at room temperature in the dark overnight. The mixture was then filtered through a pad of celite and concentrated under reduced pressure. Purification using silica gel chromatography (Eluent: Hexane/Ethyl Acetate=7:1) gave rac-6-phenyl-7-tosyl-1-oxa-7-azaspiro[4.5]dec-3-ene rac-10 as a pale yellow solid (170 mg, 0.46 mmol, 85%).

Yield 85%. $R_f$=0.60 (Hexane/Ethyl Acetate=2:1). Melting point=105-106° C.

$^1$H-NMR (300 MHz, $CDCl_3$) δ (ppm): 7.39 (d, J=8.3 Hz, 2H), 7.26-7.24 (m, 2H); 7.17-7.13 (m, 3H), 7.07 (d, J=8.1 Hz, 2H), 6.07 (dt, J=6.7 Hz, 2.5 Hz, 1H), 5.87 (d, J=6.2 Hz, 1H), 4.96 (s, 1H), 4.55 (dt, J=13.2 Hz, 2.0 Hz, 1H), 4.29 (dd, J=13.1 Hz, 2.0 Hz, 1H), 3.87-3.81 (m, 1H), 3.35 (ddd, J=13.2 Hz, 11.1 Hz, 5.1 Hz, 1H), 2.35 (s, 3H), 1.95-1.82 (m, 3H), 1.70-1.65 (m, 1H).

$^{13}$C-NMR (100 MHz, $CDCl_3$) δ (ppm): 142.8, 137.8, 137.5, 132.1, 129.3, 129.3, 127.7, 127.6, 127.2×2, 90.4, 75.4, 64.7, 41.3, 30.9, 22.5, 21.6.

FTIR (Nujol, NaCl, $cm^{-1}$): 1651, 1599, 1331, 1171.

HRMS (ESI) m/z Calcd for $C_{21}H_{24}NO_3S$ $[M+H]^+$: 370.1477. Found: 370.1480.

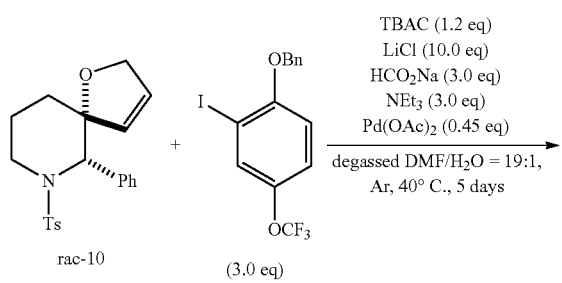

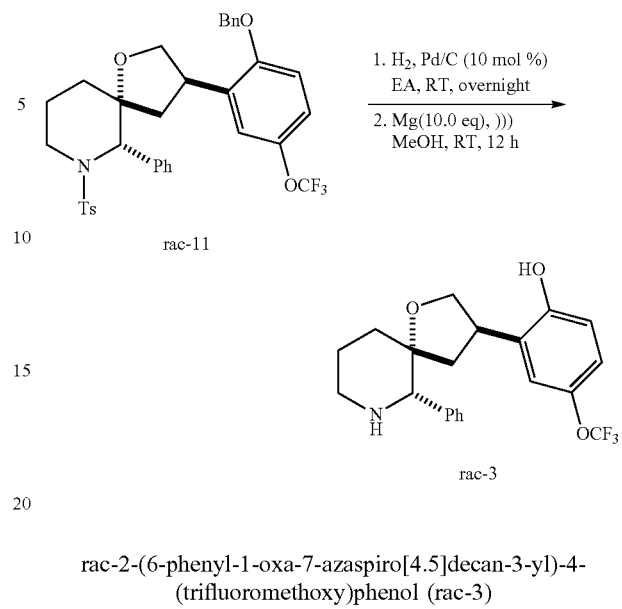

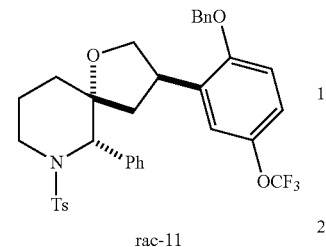

rac-11 rac-3-(2-(benzyloxy)-5-(trifluoromethoxy)phenyl)-6-phenyl-7-tosyl-1-oxa-7-azaspiro[4.5]decane (rac-11)

An oven-dried 10 mL Schlenk tube equipped with a stir bar was charged with spirocycle rac-10 (243 mg, 0.66 mmol, 1.0 eq), 1-(benzyloxy)-2-iodo-4-(trifluoromethoxy)benzene (779 mg, 1.98 mmol, 1.98 mmol, 3.0 eq), tetrabutylammonium chloride (220 mg, 0.79 mmol, 1.2 eq), lithium chloride (279 mg, 6.6 mmol, 10.0 eq), sodium formate (134 mg, 1.98 mmol, 3.0 eq), triethylamine (275 µL, 200 mg, 1.98 mmol, 3.0 eq) and a solution of DMF/H20=19:1 (2.5 mL) under Ar. The mixture was degassed in liquid $N_2$, allowed to warm to room temperature and backfilled with Ar. The degassing procedure was repeated thrice before palladium (II) acetate (66 mg, 0.30 mmol, 0.45 eq) was added and the mixture was degassed again before being heated to 40° C. and stirred for 5 days under Ar. The mixture was filtered through a pad of celite, concentrated under reduced pressure and purified using silica gel chromatography (Eluent: Hexane/Ethyl Acetate=10:1 to 6:1) to give rac-3-(2-(benzyloxy)-5-(trifluoromethoxy)phenyl)-6-phenyl-7-tosyl-1-oxa-7-azaspiro[4.5]decane rac-11 as a pale brown oil (235 mg, 0.37 mmol, 56%).

Yield 56%. $R_f$=0.68 (Hexane/Ethyl Acetate=2:1).

$^1$H-NMR (300 MHz, CDCl$_3$) δ (ppm): 7.45-7.35 (m, 5H), 7.28-7.21 (m, 4H), 7.18-7.12 (m, 4H), 7.05 (d, J=9.2 Hz, 1H), 6.97 (d, J=8.1 Hz, 2H), 6.89 (d, J=8.9 Hz, 1H), 5.13 (d, J=11.8 Hz, 1H), 5.08 (d, J=11.9 Hz, 1H), 5.02 (s, 1H), 4.20 (t, J=7.7 Hz, 1H), 3.98-3.87 (m, II-I), 3.81-3.76 (m, 2H), 3.18 (dt, J=12.2 Hz, 4.5 Hz, 1H), 2:74 (dd, J=12.6 Hz, 7.7 Hz, 1H), 2.29 (s, 3H), 2.07-2.00 (m, 2H), 1.84-1.81 (m, 2H), 1.60-1.55 (m, 1H).

$^{13}$C-NMR (125 MHz, CDCl$_3$) δ (ppm): 155.2, 142.9, 142.7, 137.7, 136.7, 136.6, 131.9, 129.5, 129.1, 128.9, 128.3, 128.0, 127.5, 127.4, 127.1, 121.0, 120.7 (q, J=254.6 Hz), 120.2, 112.6, 83.6, 72.4, 70.8, 64.2, 43.0, 41.5, 39.1, 31.6, 23.4, 21.5.

FTIR (ATR, cm$^{-1}$): 3064, 3033, 1599, 1334, 1152.

HRMS (ESI) m/z Calcd for $C_{35}H_{35}F_3NO_5S$ [M+H]$^+$: 638.2188. Found: 638.2167.

rac-2-(6-phenyl-1-oxa-7-azaspiro[4.5]decan-3-yl)-4-(trifluoromethoxy)phenol (rac-3)

The reductive Heck reaction product rac-11 (126 mg, 0.20 mmol, 1.0 eq) was dissolved in ethyl acetate (2.0 mL) before palladium on activated charcoal (10 wt %, 21 mg, 0.02 mmol, 10 mol %) was added. The round bottom flask was evacuated and refilled with H$_2$ thrice using a H$_2$ balloon. The reaction was stirred overnight at room temperature before being filtered through a pad of celite. Concentration under reduced pressure gave the crude product which was used in the next step without further purification.

The crude hydrogenation product was dissolved in anhydrous MeOH (3 mL) and magnesium powder (48 mg, 2.0 mmol, 10.0 eq) was added. The suspension was sonicated overnight and 15% aqueous HCl solution (1 mL) was added and the mixture allowed to stir for an additional 15 min before saturated aqueous NaHCO$_3$ solution was added to neutralise the mixture. Ethyl acetate (30 mL) was added and the layers separated. The aqueous phase was extracted with ethyl acetate (3×30 mL) and the combined organic extracts were washed with brine (50 mL), dried over anhydrous magnesium sulphate and filtered. Concentration under reduced pressure and purification using silica gel chromatography (Eluent: Hexane/Ethyl Acetate=2:1 to Ethyl Acetate/Methanol=2:1) to give rac-2-(6-phenyl-1-oxa-7-azaspiro[4.5]decan-3-yl)-4-(trifluoromethoxy)phenol rac-3 (40 mg, 0.102 mmol, 51%) as a pale yellow solid.

Yield=51%. $R_f$=0.32 (Ethyl Acetate/Methanol 2:1).

Melting point=203-204° C. (decomposed) (Reported as a pale yellow oil in Wallace, D. J.; Goodman, J. M.; Kennedy, D. J., Davies, A. J.; Cowden, C. J.; Ashwood, M. S.; Cottrell, I. F.; Dolling, U.-H.; Reider, P. J. Org. Lett. 2001, 3, 671-674.)

$^1$H-NMR (300 MHz, CD3OD) δ (ppm): 7.48 (dd, J=7.8 Hz, 1.6 Hz, 2H), 7.38-7.31 (m, 3H), 6.84 (dd, J=8.7 Hz, 2.0 Hz, 1H), 6.75 (d, J=2.6 Hz, 1H), 6.64 (d, J=8.7 Hz, 1H), 3.96 (t, J=7.5 Hz, 1H), 3.65 (dd, J=9.9 Hz, 8.0 Hz, 1H), 3.58 (s, 1H), 3.14-3.09 (m, 1H), 2.73 (dd, J=12.7 Hz, 2.9 Hz, 1H), 2.28-2.14 (m, 2H), 2.05-1.97 (m, 2H), 1.80-1.70 (m, 2H), 1.60 (d, J=11.9 Hz, 1H).

$^{13}$C-NMR (100 MHz, CD3OD) δ (ppm): 156.0, 142.9, 141.8, 130.4, 129.8, 129.2, 128.8, 122.2 (q, J=252.7 Hz), 121.7, 121.1, 116.6, 83.6, 72.9, 70.1, 47.7, 42.8, 40.4, 38.7, 24.6.

FTIR (ATR, cm$^{-1}$): 3290, 3062, 3032, 1607, 1510, 1494.

HRMS (ESI) m/z Calcd for $C_{21}H_{23}F_3NO_3$ [M+H]$^+$: 394.1630. Found: 394.1611.

The invention claimed is:

1. Method for synthesizing a compound of Formula (II)

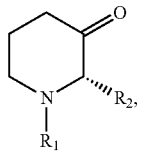
(II)

wherein $R_1$ is a nitrogen-protecting group derivable from an amino group selected from the group consisting of tosylamide (Ts), t-butyl carbamate (Boc), benzyl carbamate (Cbz), 9-fluorenylmethyl carbamate (Fmoc), acetamide (Ac), trifluoroacetamide (TFA), benzylideneamine, triphenylmethylamine (Tritylamine), benzylamine (Bn), and phthalimide;

$R_2$ is selected from the group consisting of halogen, —C(O)—R, —NRR', —OR, —SR, —COOR, —CN, —NO$_2$, —C(O)—NRR', —NR'—C(O)—R, —SO$_2$—R, —(SO$_2$)—OR, linear or branched, substituted or unsubstituted $C_1$-$C_{10}$ alkyl; linear or branched, substituted or unsubstituted $C_2$-$C_{10}$ alkenyl; linear or branched, substituted or unsubstituted $C_2$-$C_{10}$ alkynyl; linear or branched, substituted or unsubstituted $C_1$-$C_{10}$ alkoxy; substituted or unsubstituted $C_3$-$C_{10}$ cycloalkyl; substituted or unsubstituted $C_3$-$C_{10}$ cycloalkenyl; substituted or unsubstituted $C_6$-$C_{10}$ aryl; substituted or unsubstituted $C_3$-$C_{10}$ heteroaryl;

R and R' are independently selected from the group consisting of H and linear or branched, substituted or unsubstituted $C_1$-$C_{10}$ alkyl;

the method comprising:

reacting a compound of Formula (I)

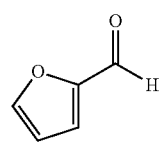
(I)

with NH$_2$R$_1$ to form a compound of Formula (IV)

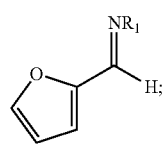
(IV)

reacting the compound of Formula (IV) with a precursor of R$_2$ in the presence of a rhodium catalyst to form an enantiomer of a compound of Formula (V)

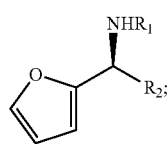
(V)

reacting the compound of Formula (V) with an oxidizing agent to form a compound of Formula (VI)

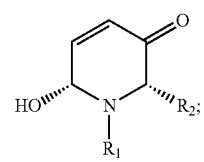
(VI)

reacting the compound of Formula (VI) with a reducing agent to form a compound of Formula (VII)

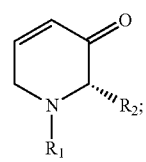
(VII)

and hydrogenating the compound of Formula (VII) to form the compound of Formula (II).

2. Method according to claim 1, wherein $R_1$ is a nitrogen-protecting group derivable from an amino group selected from the group consisting of Ts, Boc, and Bn.

3. Method according to claim 2, wherein $R_1$ is a nitrogen-protecting group derivable from Ts.

4. Method according to claim 3, wherein said reacting the compound of Formula (I) with NH$_2$R$_1$ to form the compound of Formula (IV) comprises reacting the compound of Formula (I) with tosylamide in presence of a Lewis acid.

5. Method according to claim 4, wherein the Lewis acid is boron trifluoride diethyl etherate (BF$_3$.O(Et)$_2$) or para-toluenesulfonic acid (PTSA).

6. Method according to claim 1, wherein $R_2$ is selected from the group consisting of linear or branched, substituted or unsubstituted $C_1$-$C_{10}$ alkyl, and substituted or unsubstituted $C_6$-$C_{10}$ aryl.

7. Method according to claim 6, wherein $R_2$ is substituted or unsubstituted $C_6$-$C_{10}$ aryl.

8. Method according to claim 7, wherein $R_2$ is substituted or unsubstituted phenyl.

9. Method according to claim 8, wherein said precursor of $R_2$ is triphenylcyclotriboroxane ((PhBO)$_3$) or is any one of the following:

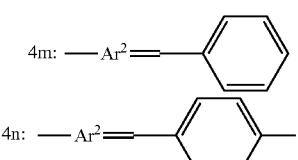

-continued

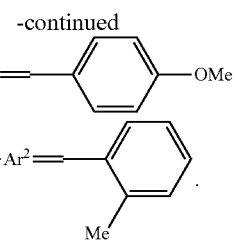

10. Method according to claim 9, wherein said rhodium catalyst is chlorobis(ethylene)rhodium(I) dimer ([RhCl(C$_2$H$_4$)]$_2$).

11. Method according to claim 1, wherein said oxidizing agent is selected from the group consisting of N-bromosuccinimide (NBS), meta-chloroperoxybenzoic acid (MCPBA), bromine in methanol, and titanium isopropoxide (Ti(OiPr4)) with tert-butyl hydroperoxide (TBPH).

12. Method according to claim 1, wherein said reducing agent is selected from the group consisting of triethylsilane (Et$_3$SiH), dimethylethylsilane, dimethylphenylsilane, dimethylbenzylsilane, and diethyoxymethylsilane.

13. Method according to claim 1, wherein said hydrogenating the compound of Formula (VII) to form the compound of Formula (II) comprises reacting the compound of Formula (VII) with hydrogen in presence of a palladium on carbon (Pd/C) catalyst.

14. Method according to claim 1, wherein the compound of Formula (II) is

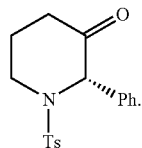

(tosyl-protected (2S)-phenyl-3-piperidone)

* * * * *